United States Patent [19]

von der Ohe et al.

[11] 4,263,282

[45] Apr. 21, 1981

[54] LH-RH-PEPTIDES AS CONTRACEPTIVES

[75] Inventors: Marianne von der Ohe, Wiesbaden; Jürgen K. Sandow, Königstein; Wolfrad von Rechenberg, Kelkheim, all of Fed. Rep. of Germany

[73] Assignee: Hoechst Aktiengesellschaft, Frankfurt am Main, Fed. Rep. of Germany

[21] Appl. No.: 96,029

[22] Filed: Nov. 20, 1979

Related U.S. Application Data

[63] Continuation-in-part of Ser. No. 930,651, Aug. 6, 1977, abandoned.

[30] Foreign Application Priority Data

Aug. 6, 1977 [DE] Fed. Rep. of Germany ....... 2735515

[51] Int. Cl.$^3$ ............................................. A61K 37/00
[52] U.S. Cl. .................................................. 424/177
[58] Field of Search ......................................... 424/177

[56] References Cited

U.S. PATENT DOCUMENTS

| | | | |
|---|---|---|---|
| 3,928,307 | 12/1975 | Foell et al. | 424/177 |
| 4,010,256 | 3/1977 | Parlow | 424/177 |
| 4,010,261 | 3/1977 | Johnson et al. | 260/112.5 LH |
| 4,024,248 | 5/1977 | Konig et al. | 260/112.5 LH |
| 4,034,082 | 7/1977 | Johnson et al. | 260/112.5 |
| 4,118,483 | 10/1978 | Konig et al. | 424/117 |

*Primary Examiner*—Frederick E. Waddell
*Attorney, Agent, or Firm*—Curtis, Morris & Safford

[57] ABSTRACT

What is disclosed in a method of inducing a contraceptive effect in a mammal by administering a contraceptively effective amount of a peptide of the formula

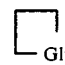
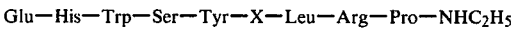

Glu—His—Trp—Ser—Tyr—X—Leu—Arg—Pro—NHC$_2$H$_5$ in which X stands for D-serine-tert.butyl ether or D-glutamic acid γ-cyclohexylamide.

2 Claims, No Drawings.

LH-RH-PEPTIDES AS CONTRACEPTIVES

This application is a continuation-in-part of application Ser. No. 930,651 filed Aug. 6, 1977 and now abandoned.

This invention relates to the use of peptides of the formula

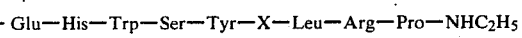

in which X denotes D-serine-tert.butyl ether or D-glutamic acid γ-cyclohexylamide as contraceptives.

The aforementioned compounds are prepared by the processes disclosed in U.S. Pat. No. 4,024,248 and U.S. Pat. No. 4,118,483. In test persons a single dose of 1.4 to 20 mcg (corresponding to 20 to 300 ng/kg) administered intravenously (i.v.), subcutaneously (s.c.) or by the intramuscular route (i.m.) or of 50 to 1,000 mcg (corresponding to 100 to 5,000 ng/kg) administered intranasally (i.n.) causes the secretion of gonadotrophic hormones from the anterior lobe of the pituitary gland.

It has now been found that repeated doses of more than 2.5 mcg i.v., s.c. or i.m. (daily dose) or over about 100 mcg i.n. over a period of at least 4 days do not increase the effect but, surprisingly, that the effect is reversed so that the aforesaid compounds can be used as contraceptives when administered in appropriate doses to male and female mammals.

The mechanism of this effect may be explained as follows: The compounds administered have a strong effect on the release of gonadotrophins from the pituitary gland and also stimulate the synthesis of these hormones. In chronic treatment with sufficiently high dosages a discrepancy between release and synthesis will eventually arise so that the release of gonadotrophic hormones will be diminished or even be practically abolished. The time interval in which this occurs depends on the dose of the compound administered. Small amounts of the compounds administered over limited periods of time are therefore able to bring about ovulation while chronic treatment in dosages over 2.5 mcg i.v., s.c. or i.m. will suppress ovulation.

The dosage of the compound wherein X is D-serine-tert.butyl ether, for example, is three times 5 mcg s.c., i.v. or i.m. per day. It may be further increased without hesitation to a multiple as the peptides of the aforementioned general formula are non-toxic. In such case, however, the specific advantage of the compound which is effective in very low dosages is given away. In practice, the daily dosage is in the range of from 5 to 500 mcg. However, the more preferred dosage is 2.5 to 50 mcg per person corresponding to about 0.05 to 1.0 mcg/kg. A higher dose is less advantageous because it can lead to unwanted side effects such as atrophy of the genital organs in men and women. Furthermore the limited solubility of the compounds precludes the use of higher doses. Because of a resorption of about only 1% with intranasal administration, the dosage in this case must be increased to about a hundredfold. Thus the nasal dose is about 100 to 2000 mcg per person corresponding to 2 to 40 mcg/kg.

Hence, when administered in this way, the compounds can be used in men to cause a temporary suppression of testosterone production and, consequently, of sperm formation and, in women, they suppress ovulation. The administration to women starts, for example, on the first day of the cycle and it is continued for about 14 days. In this manner, ovulation during the time of treatment is suppressed with certainty. The LH-level drops to basal values and a stimulation of the pituitary gland is no longer possible. Hence, ovulation can be deferred by a short time treatment and it can be suppressed by a treatment over a longer period of time. With a long term treatment nidation may also be suppressed as both processes depend on the height of the FSH and LH level.

Hitherto, attempts have been made to suppress the LH and FSH release by using competitive inhibitors of LH-RH. This has been possible to an unsatisfactory extent only and the required concentrations have been approximately a thousand times higher than the amount of the peptides to be used according to the invention.

Moreover, the problems of residues and metabolism to be considered, for example with steroid-containing contraceptives, do not arise. The preparations to be used according to the invention contain peptides which are easily decomposed in the human body into amino acids which are discharged or metabolized in a physiological manner.

Compounds of the aforementioned general formula can be administered parenterally in physiological sodium chloride solution, i.e. by intravenous, intramuscular or subcutaneous injection. For long term treatment it proved especially useful to administer aqueous or oily preparations intranasally. Alternatively, rectal or vaginal administration in the form of suppositories is possible.

(a) Observation in men 50 mcg per day of the compound wherein X is D-serine-tert.butyl ether in aqueous preparation were administered subcutaneously for 10 days to three men at the age of 30 to 55. The testosterone level was measured by radio-immuno assay. It was found that the testosterone level in the plasma had dropped to about one third of the initial value. 6 Weeks after the end of the treatment the testosterone level was again measured and it was found that the initial values had been reached again. The same results were obtained by intranasal administration of daily doses of 2 mg in an oily preparation for 10 days.

(b) Observation in women

From the beginning of the cycle, 5 mcg of the compound wherein X is D-serine-tert.butyl ether were administered 3 times per day subcutaneously in aqueous preparation to 4 women at the age of 22 to 30. A few days after the treatment the plasma level of luteinizing and follicle-stimulating hormone had dropped to basal values and a stimulation of the hypophysis no longer occured.

With a short term treatment, ovulation was deferred, whereas with a long term treatment it was suppressed completely.

(c) Observation in animals

One daily dose of 2.5 mcg/kg of the compound wherein X is D-serine-tert.butyl ether was injected subcutaneously in isotonic sodium chloride solution to 2 groups, each of 5 sexually mature, purebred male beagles having a weight of 6 to 8 kg. After one month, the testosterone level dropped to 30% of the initial value; after 3 months it had reached 6% of the initial value. The treatment was continued for 6 months. During the course of the treatment a marked atrophy of the testicles was observed, but 8 weeks after the discontinuation of the treatment the size of the testicles had distinctly increased again and the animals showed a normal libido.

The following examples illustrate the invention.

EXAMPLE 1

500 mg of that compound wherein X is D-serine-tert.-butyl ether are dissolved in 100 liters of physiological sodium chloride solution. The solution is filtered under sterile conditions and filled into 1 ml ampules. The preparation can be used for intravenous, intramuscular or subcutaneous administration of this compound or, quite generally, of either compound of the aforementioned general formula.

EXAMPLE 2

600 mg of compound that compound in which X is D-glutamic acid δ-cyclohexylamide are dissolved in 100 liters of isotonic aqueous mannitol solution and further treated as described in Example 1. The solution filled into ampules is lyophilized and for use it is redissolved in distilled water.

EXAMPLE 3

9 Liters of distilled water are heated to boiling and 20 g of 4-hydroxybenzoic acid methyl ester are dissolved therein. The solution is cooled to about 30° C., 89.6 g of $Na_2HPO_4$, 13.5 g of citric acid, 10 g of sodium chloride. and 250 g of mannitol are added and 100 g of that compound wherein X is D-serine-tert. butyl ether are dissolved in the mixture. The whole is made up to 10 liters with distilled water and filtered.

1 ml of the solution is introduced, for example, into a container provided with a dosing valve discharging 0.05 ml per administration.

EXAMPLE 4

10 g of benzyl alcohol are made up to 0.990 liter by means of 2-octyldodecanol, 10 g of microfinely ground compound wherein X is D-serine-tert.butyl ether are added and the whole is homogenized.

1 to 2 ml of the suspension obtained are filled into small comtainers provided with dosing valves discharging 0.05 ml of suspension per administration.

EXAMPLE 5

2 kg of commercial base for suppositories is heated to about 60° C., 2 mg or microfinely ground compound wherein X is D-serine-tert.butyl ether are added and the whole is homogenized. The mass is poured into moulds and after cooling the suppositories each having a weight of 2 g are released.

EXAMPLE 6

Glu—His—Trp—Ser—Tyr—D—Gln(cyclohexyl)—Leu—Arg—Pro—NH—$C_2H_5$ (a) Z-D-Gln(cyclohexyl)-OBzl 7.35 g of dicyclohexyl-carbodiimide (DCC) are added at 0° C. to a solution of 12.3 g (33.1 mols) of Z-D-Glu-OBzl, 4.06 ml (33.1 mols) of cyclohexylamine and 4.47 g of 1-hydroxybenzotriazole (33.1 mols) in 50 ml of absolute tetrahydrofuran. The whole is left to stand for 2 hours at 0° C. and overnight at room temperature. The following day the precipitate is filtered off with suction, washed with tetrahydrofuran and the filtrate is concentrated. The residue is rubbed with saturated $NaHCO_3$ solution, the mixture is filtered off with suction, the residue is thoroughly washed with water and dried. Yield 14.5 g, melting point 105° C. After recrystallization from isopropanol/petroleum ether, the yield amounts to 6 g, melting point 163° C., $[\alpha]_D^{20} = +1°$ (c=1, in glacial acetic acid).

(b) Z-D-Gln(cyclohexyl)-OH 6 g of Z-D-Gln(cyclohexyl)-OBzl are suspended in 100 ml of dioxane/water (4:1) and titrated with 1N NaOH (thymolphthalein as indicator, consumption 14 ml 1N NaOH). Next, the mixture is neutralized with 1N HCl and concentrated in vacuo. The residue is partitioned between ethyl acetate and 1N HCl. The ethyl acetate phase is washed with water, dried and concentrated. The residue is rubbed with ether and filtered with suction. Yield 4.3 g, melting point 112° to 115° C., $[\alpha]_D^{20} = +6.2°$ (c=1, in methanol).

(c) H-Ser-Tyr-D-Gln(cyclohexyl)-Leu-Arg-Pro-NH-$C_2H_5$.2 HCl 1.3 ml of N-ethylmorpholine and 1.1 g of DCC are added at 0° C. to a solution of 1.89 g (5 mmols) of Z-D-Gln(cyclohexyl)-OH, 3.6 g (5 mmols) of H-Leu-Arg-Pro-NH-$C_2H_5$-ditosylate and 1.35 (10 mmols) of 1-hydorxybenzotriazole in 20 ml of dimethyl formamide. The mixture is stirred for 1 hour at 0° C. and left to stand overnight at room temperature.

The reaction product precipitates together with dicyclohexyl urea. Ether is added to the reaction mixture and the precipiitate is filtered off with suction. The filter cake is rubbed with saturated $NaHCO_3$ solution and filtered off with suction. Yield: 3.2 g of an amorphous mass which is catalytically hydrogenated as described in Example 1d of U.S. Pat. No. 4,118,483 in methanol in the presence of a palladium catalyst. When the hydrogenation is complete, the catalyst is filtered off with suction, the filtrate is concentrated and the residue is rubbed with ether. Yield: 2.2 g of an amorphous mass which is dissolved, without further purification, in a small amount of dimethyl formamide together with 1.5 g of Z-Ser-Tyr-(Bzl)-OH and 405 mg of 1-hydroxy-benzotriazole. 0.78 ml of N-ethylmorpholine is added to the solution obtained and 660 mg of DCC are then added at 0° C. The precipitate is filtered off with suction and the filtrate is concentrated. The residue is rubbed with saturated $NaHCO_3$ solution, filtered off with suction and washed with water. Yield: 2.6 of an amorphous mass which is catalytically hydrogenated without purification in a mixture of dimethyl formamide and methanol (1:1). When the hydrogenation is complete, the catalyst is filtered off with suction, the residue is rubbed with ether and then purified by partition chromatographpy. Yield: 420 mg of a uniform (thin layer chromatogram), ninhydrin-positive compound with correct amino acid analysis. (solvent 1)

d) 

215 mg of

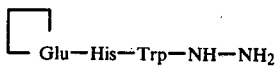

are reacted as described in Example 1f of U.S. Pat. No. 4,118,483 with 420 mg of H-Ser-Tyr-D-Gln(cyclohexyl)-Leu-Arg-Pro-NH-C$_2$H$_5$.2 HCl and transformed into the acetate. The compound is purified by gradient elution on a carboxymethyl cellulose column (11×1.5 cm) with 0.002 to 0.01 N ammonium acetate buffer as eluant. 128.3 mg of a uniform (thin layer chromatography) product are isolated (solvent 1). According to the ultraviolet spectrum and amino acid analysis, the content of peptide base is found to be 80%. The remainder is water (10%) and acetic acid (10%). $[\alpha]_D^{20} = -33.4°$ (c=1, in water).

Amino acid analysis (hydrolysis for 68 hours in 6N HCl at 110° C.: Ser (0.7), Glu (2.0), Pro (0.9), Leu (1.0), Tyr (0.9), His (1.0), Arg (1.0). The Trp-content is determined by UV extinction (1.0).

What is claimed is:

1. The method of inducing a contraceptive effect in a male of female patient which comprises parenterally administering to said patient, over a period of at least four days, a daily dose from 0.05 to 1.0 micrograms per kilogram of body weight of a peptide of the formula Glu-His-Trp-Ser-Tyr-X-Leu-Arg-Pro-NHC$_2$H$_5$ wherein X is D-serine-tert.butyl ether or D-glutamic acid δ-cyclohexyl amide.

2. The method of inducing a contraceptive effect in a male or female patient which comprises intranasally administering to said patient, over a period of at least four days, a daily dose from 2 to 40 micrograms per kilogram of body weight of a peptide of the formula Glu-His-Trp-Ser-Tyr-X-Leu-Arg-Pro-NHC$_2$H$_5$, wherein X is D-serine-tert.butyl ether or D-glutamic acid δ-cyclohexyl amide.

* * * * *

UNITED STATES PATENT AND TRADEMARK OFFICE
CERTIFICATE OF CORRECTION

PATENT NO. : 4,263,282
DATED : April 21, 1981
INVENTOR(S) : von der Ohe et al.

It is certified that error appears in the above-identified patent and that said Letters Patent are hereby corrected as shown below:

In the Heading, Item [63], "Aug. 6, 1977" should read --Aug. 3, 1978--;

Column 1, line 5, "Aug. 6, 1977" should read --Aug. 3, 1978--.

Column 6, line 16 and 26 (Claims 1 and 2), "Glu..." should read --⌐Glu...--.

Signed and Sealed this

Eleventh Day of August 1981

[SEAL]

Attest:

Attesting Officer

GERALD J. MOSSINGHOFF

Commissioner of Patents and Trademarks